United States Patent
Hsieh et al.

(10) Patent No.: US 6,359,956 B1
(45) Date of Patent: Mar. 19, 2002

(54) RECONSTRUCTION IN HELICAL COMPUTED TOMOGRAPHY USING ASYMMETRIC MODELING OF DETECTOR SENSITIVITY

(75) Inventors: Jiang Hsieh, Brookfield; Jianying Li, New Berlin, both of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/739,027

(22) Filed: Dec. 15, 2000

(51) Int. Cl.⁷ .............................................. A61B 6/03
(52) U.S. Cl. ........................... 378/15; 378/4; 382/131
(58) Field of Search ....................... 378/4, 15, 901; 382/131

(56) References Cited

U.S. PATENT DOCUMENTS

| | | | |
|---|---|---|---|
| 5,265,142 A | * 11/1993 | Hsieh | 378/4 |
| 5,270,923 A | * 12/1993 | King et al. | 382/131 |
| 5,606,585 A | * 2/1997 | Hu | 378/15 |
| 6,091,840 A | * 7/2000 | Hu et al. | 378/15 |

* cited by examiner

Primary Examiner—Robert H Kim
Assistant Examiner—Drew A. Dunn
(74) Attorney, Agent, or Firm—Quarles & Brady LLP

(57) ABSTRACT

Helical acquisition of thin computed tomography slices by collimation of the fan beam to less than the width of a multi-row detector is provided by interpolation after application of the weighting scheme correcting for asymmetry in the detector profile of the detectors with such collimation.

24 Claims, 1 Drawing Sheet

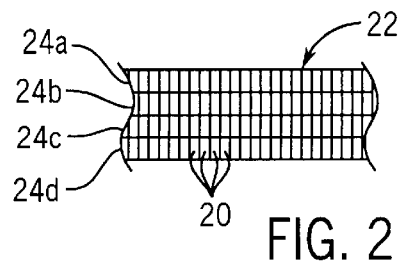
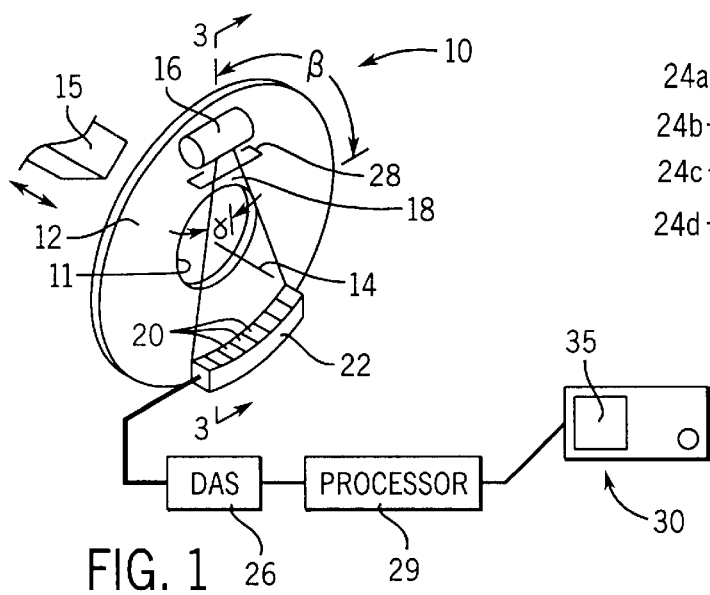
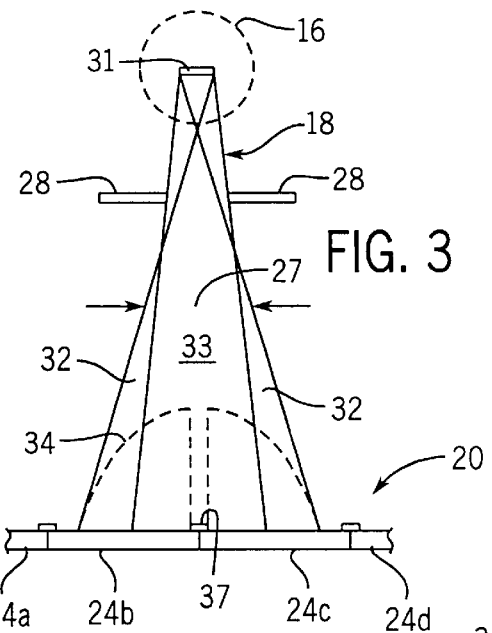
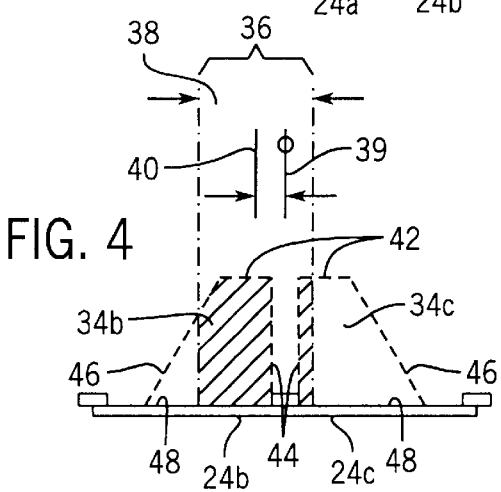
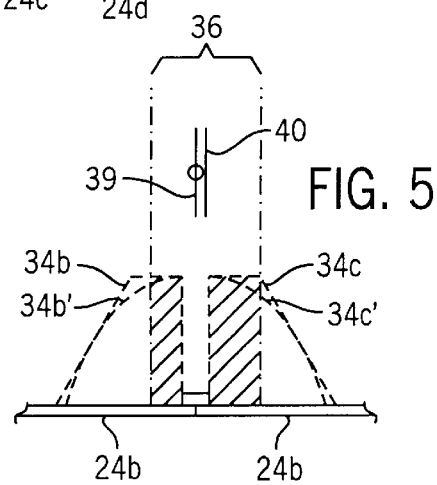

RECONSTRUCTION IN HELICAL COMPUTED TOMOGRAPHY USING ASYMMETRIC MODELING OF DETECTOR SENSITIVITY

FIELD OF THE INVENTION

The present invention relates to x-ray computed tomography using helical scanning and specifically to a reconstruction technique for helical scanning providing improved slice interpolation.

BACKGROUND OF THE INVENTION

X-ray computed tomography is a well-known procedure for creating cross-sectional images from computer processed x-ray projections taken along the plane of the cross section. In a typical CT machine, an x-ray tube is mounted on a rotatable gantry to project the fan beam of x-rays at a patient through a "slice" from a variety of angles. The x-rays are received after passing through the patient by a multi-element detector to provide a measurement of x-ray attenuation along a variety of rays of the fan beam. The attenuation signals from the elements of the multi-element detector are sampled and digitized by a data acquisition system.

Digitized projections collected at a range of angles about the patient, typically no less than 180° plus half the fan beam angle, are collected in as a "tomographic projection set" and reconstructed according to well known techniques in the art, such as filtered back projection, into an image of a cross section of the patient along that slice. Volumetric images may be obtained by taking a series of adjacent slices to permit three-dimensional modeling of structures within the patient or to permit arbitrary changes in the cross-sections obtained.

The time required to obtain one or more tomographic projection sets may be shortened by simultaneously rotating the gantry and moving of the patient along the gantry's axis of rotation. This technique is termed "helical scanning" because the path of the x-rays follows a helix about the patient.

In helical scanning, the projections of the tomographic projection set do not lie in a single plane, a condition necessary for tomographic reconstruction. Accordingly, the projections may be interpolated to a common and arbitrarily chosen "slice plane". Actual projections taken at common angles but displaced on either side of the slice plane later or earlier in the helical scan are used as end points in the interpolation. The interpolated data may then be reconstructed according to conventional techniques.

Additional increases in the speed of acquisition may be obtained by providing the multi-element x-ray detector with several rows displaced from one another along the axis of rotation of the gantry. In this way, multiple tomographic projections can be acquired at a given time. Using such a multi-row x-ray detector, interpolation to a single image plane may be accomplished by using projections acquired by different rows within the detector at a single gantry position.

At certain times, it may be desirable to acquire tomographic projections of extremely thin slices. The slice thickness can be controlled by collimating the fan beam to an arbitrary axial dimension limited only by minimum scan speeds and acceptable signal to noise ratio. Importantly, the axial dimension of the fan beam may be less than the axial dimension of the multi-element x-ray detector or a single row of a multi-row x-ray detector. This preserves the ability of the CT machine to also image thicker slides.

Although adjusting the collimator to obtain thin slices, each narrower than a row of the x-ray detector, works well for non-helical scanning, when this technique is used in conventional helical scanning, unacceptable image artifacts are produced.

BRIEF SUMMARY OF THE INVENTION

The present inventors have recognized that producing thin slices by collimation of the fan beam can produce a variation in effective x-ray sensitivity across the axial dimension of the detector rows. This variation is caused principally by a penumbra at the edges of the collimated x-ray beam. This variation, in turn, introduces a nonlinearity to the interpolation process used in helical scanning, which, if uncorrected, can introduce artifacts to the image.

Accordingly, the present invention provides a correcting weighting to the interpolation of helically acquired data to a single slice plane. Generally the weighting considers the degree of overlap of the desired slice with asymmetric detector profiles of the two detectors. The weighting compensates for nonlinear variations in the overlapped area as a function of slice location.

Specifically, the present invention provides a method of data acquisition for a computed tomography machine having an opposed x-ray source and a multi-row x-ray detector mounted on a gantry for helical rotation about a patient along a longitudinal axis. Longitudinal variation in x-ray detection across the rows of the multi-row x-ray detector are determined and the detector is used to acquire a set of tomographic projection data at angles about the patient over a helical path. A slice having a location and thickness for tomographic reconstruction is selected. Then, for each of the rows, the data of the detector elements of the rows are weighted according to the modeled variation in x-ray detection of the row and according to an overlap of the slice with the row. The weighted data is reconstructed.

In the following description, reference is made to the accompanying drawings, which form a part hereof, and in which there is shown by way of illustration, a preferred embodiment of the invention. Such embodiment also does not define the scope of the invention and reference must be made therefore to the claims for this purpose.

BRIEF DESCRIPTION OF THE DRAWINGS

FIG. 1 is a simplified block diagram of a CT system having a rotatable gantry and axially movable table suitable for helical scanning showing an x-ray tube and detector opposed about the gantry bore, and showing the signal path from the detector to a processor used to reconstruct tomographic images according to input from an operator console;

FIG. 2 is a top plan view of the detector of FIG. 1 showing multiple detector elements arranged in axially spaced rows;

FIG. 3 is a simplified cross-sectional view of the gantry of FIG. 3 taken along line 3—3 and showing the x-ray path from the x-ray source to a collimator to adjacent rows of the detector and the unsymmetrical detector profiles produced by a penumbra effect of the collimation;

FIG. 4 is a detail view similar to that of FIG. 3 showing super position of a reconstruction slice over two trapezoidal model detector profiles at a first position for interpolation; and FIG. 5 is a view similar to that of FIG. 4 showing interpolation at a different position of a slice plane and the effect of asymmetry of the interpolation calculation.

DETAILED DESCRIPTION OF THE INVENTION

Referring now to FIG. 1, an x-ray computed tomographic system 10 may include an annular gantry 12 rotatable around a longitudinal axis of rotation 14 centered within the opening 11 of the annular gantry 12. The gantry may rotate about the axis of rotation 14 through angles β. A patient may be supported on a table 15 for movement through the opening 11 of the gantry 12 longitudinally. As is understood in the art, the table movement may occur simultaneously with rotation of the gantry 12 for helical scanning operations.

One edge of the gantry supports an x-ray source 16 oriented to project an x-ray fan beam 18 across the opening 11 of the gantry 12 so that a broad surface of the fan beam 18 is normal to the axis of rotation 14. The fan beam 18 is defined in longitudinal thickness by collimator blades 28 and extends generally from a focal spot within the x-ray source 16 along a number of rays defined by angles 7 to be receive by individual detector elements 20 of rows of multi-row detector 22 positioned opposite the opening 11 from the x-ray source 16. Referring also to FIG. 2, the multi-row detector 22 arranges individual detector elements 20 in longitudinally spaced rows 24 extending generally along the plane of the gantry 12.

Referring again to FIG. 1, x-ray attenuation signals from each of the detector elements 20 in each of the rows 24 are received by a data acquisition system 26 of a type well known in the art, which samples and digitizes the signals so as to provide digital attenuation values to a processor 29. The processor 29 also receives input signals from a console 30, through which, for example, an operator may indicate desired slice locations and thicknesses at which tomographic images will be generated. In turn, the console 30 may receive tomographic images at the desired slice locations for display on a console screen 35.

Referring now to FIG. 3, the axial dimension 27 of the fan beam 18 may be controlled by adjustment of the collimator blades 28 toward or away from each other so as to define an aperture through which x-rays may pass. For thin slices, the collimator blades 28 may be adjusted close to each other so that x-rays passing from the focal spot 31 of the x-ray source 16 to the rows 24 of the multi-row detector 22 strike only two rows 24 designated in FIG. 3 as rows 24b and 24c.

As a result of the finite axial extent of a focal spot 31 within the x-ray source 16, a penumbra region 32 will be created at the axial edges of the fan beam 18 near the outer edges of rows 24b and 24c. The penumbra region 32 surrounds an unoccluded area 33 centered at the interface between rows 24b and 24c. The falling off of x-ray flux in the penumbra region 32 creates an effective decrease in sensitivity of the detector elements 20 in these regions as is reflected in a detection profile 34 having downward sloping axial outer edges. A tungsten occluder 37, fitting between adjacent rows 24, creates a relatively sharp boundary in the detector profile 34 at the inner edges of rows 24b and 24c.

The contrast between the axially outer sloping edges of the profile 34 in the penumbra regions 32 and the sharp vertical inner edges of the profile 34 in the unoccluded area 33 creates an asymmetry in detection profile 34 that contrasts with the generally rectangular detection profile seen when the multi-row detector 22 is fully illuminated with an axially wider fan beam 18.

Referring now to FIG. 4, the asymmetric detector profile 34a of detector row 24b and detector profile 34c of detector row 24c will overlap by a varying amount, depending on the point of data acquisition within a helical scan, with an interpolation target slice 36 at a desired location for a tomographic image. The interpolation target slice 36 generally has a width 38 and a center plane 40.

As the center plane 40 of the interpolation target slice 36 moves relative to the center 39 of the rows 24b and 24c, the areas of the detector profiles 34b and 34c overlapping with the interpolation target slice 36 will change as a nonlinear function of that movement. This nonlinearity results from the sloping portion of the profile 34 and would not occur if profile 34c and 34b were rectangular as occurs with thicker fan beam collimation.

For example, as depicted in FIG. 4, profiles 34b and 34c may modeled as trapezoids having upper bases 42 that are generally horizontal and subtend the unoccluded area 33 of the fan beam, inner faces 44 that are generally vertical and outer faces 46 within the penumbra regions 32 of the fan beam 18 that slope downwardly outward toward larger lower bases 48. At the depicted location of the interpolation target slice 36, a leftmost edge of the interpolation target slice 36 overlaps the sloping edge of the detector profile 34b whereas a rightmost edge of the interpolation target slice 36 overlaps a horizontal portion of detector profile 34a. In this case, a rightward relative movement of the interpolation target slice 36 will cause a linearly related increase in overlapped area of profile 34c as the leading edge of the interpolation target slice 36 travels along the horizontal upper base 42 of profile 34c. However, the amount of area of profile 34b overlapped by the interpolation target slice 36 will not decrease linearly but will decrease quadratically as a result of the travel of the trailing edge of interpolation target slice 36 up the sloping face of the profile 34b. Accordingly, a simple linear interpolation between the signals detected by rows 24b and 24c based on a single center point of the rows 24b and 24c to the center plane 40 of the interpolation target slice 36 will provide incorrect weightings to the two signals for most situations where the axial edges of the interpolation target slice 36 straddle one of faces 46 of the two detector rows 24 between which interpolation will be conducted.

In contrast, as shown in FIG. 5, when both the leftmost edge of the interpolation target slice 36 and the right most edge of the interpolation target slice 36 overlap a horizontal portion of detector profiles 34b and 34c, the amount of area of profile 34b and 34c returns to a linear relationship with relative movement between centers 39 and 40.

Both of these cases can be accommodated if the contribution of each of the detector elements 20 in rows 24b and 24c to a given interpolation target slice 36 is made to reflect the actual area of the detector profiles 34 subtended by the axial dimension of the interpolation target slice 36 indicated by cross-hatching in FIG. 4. This may be accomplished by the use of linear interpolation with a pre-weighting of the signals from the detector elements 20 of rows 24b and 24c prior to interpolation to accommodate the asymmetry of these profiles 34. This may be done by modeling the detector profiles 34b and 34c and calculating the overlap as a function of displacement of centers 39 and 40 and using this calculation as a pre-weighting.

Generally the processor 29 may implement the weighting described above as well as the interpolation and the reconstruction. Since backprojection is essentially a summation process, the weighted projections are summed during the backprojection to complete the interpolation process. Alternatively, the projections can be first interpolated prior to the tomographic reconstruction.

Referring to FIG. 5, other models may also be used including a Gaussian model producing profiles 34b' and 34c' or a template being an actual empirically determined profile, by making measurements with differently placed occluders over ones of rows 24b and 24c and fractions thereof, may be used.

EXAMPLE 1

For a CT machine providing a helical pitch of 1.5 to 1 meaning that the patient progresses 1.5 times the axial dimension of the full-width-at-half-maximum of one collimated detector for each rotation of the gantry 12 and using the trapezoidal approximation of the profiles 34b and 34c as shown in FIG. 4, a pre-weighting for signals of row 34b may be as follows and for row 34c may be as follows:

$$w_1(\gamma, \beta) = \begin{cases} 3\theta_1^2 - 2\theta_1^3, & \beta_1 - 2\pi/3 \le \beta < \beta_1 \\ \dfrac{\beta_2 - \pi - 2\gamma - \beta}{\beta_2 - \pi - 2\gamma - \beta_1} & \beta_1 \le \beta < \beta_2 - \pi - 2\gamma \\ 0 & \text{otherwise} \end{cases} \quad (1)$$

$$w_2(\gamma, \beta) = \begin{cases} \dfrac{\beta - \beta_1 - \pi + 2\gamma}{\beta_2 - \beta_1 - \pi + 2\gamma} & \beta_1 + \pi - 2\gamma \le \beta < \beta_2 \\ 3\theta_2^2 - 2\theta_2^3, & \beta_1 \le \beta < \beta_2 - \pi - 2\gamma \\ 0 & \text{otherwise} \end{cases} \quad (2)$$

$$\theta_1 = \frac{\beta - \beta_1 + 2\pi/3}{2\pi/3}, \quad \text{and} \quad \theta_2 = \frac{\beta_2 + 2\pi/3 - \beta}{2\pi/3}.$$

Where β is the projection view angle, and β1 and β2 are the projection angles when the center of the reconstruction slice is aligned with the center of the two detector rows, respectively. The weights may be multiplied by the measured signals from the detectors of rows 24b and 24c and the products are used for reconstruction using any available reconstruction algorithms. Thus the weights handle both the asymmetry and the interpolation in one step.

It will be understood to those of ordinary skill in the art that the weighting for asymmetry correction can be either be incorporated as weighting prior to the standard reconstruction process or be used as the weights for interpolation. The interpolated samples are then used for FBP. Thus as used herein, the step of applying a weighting for the purpose of correction for variation in detector profile and interpolation should be considered met by systems that accomplish this as two steps with two weightings or one step with a combined weighting.

The invention thus provides a correction for helical interpolation useful in any situation where the detectors exhibit a longitudinal variation in detection either because of variations in the x-ray fan beam or variations in the sensitivity of the detectors themselves. By using a trapezoid, a Gaussian curve or may be a stored template as a model, an arbitrary precision in the correction according to the desired complexity of the model. The trapezoidal model is easy to store and provides for simple calculation of the weights. A Gaussian model provides greater fidelity in drop-off of the x-ray beam under conditions of scatter with the cost of more complex weighting. Measured and stored templates, acquired under various conditions of occlusion of the detector, can compensate for more complex variations. When the slice thickness may be less than a longitudinal dimension of one row of the detector the invention accommodates the penumbra effects of collimation of the x-ray beam to narrow fans.

The foregoing objects and advantages may not apply to all embodiments of the inventions and are not intended to define the scope of the invention, for which purpose claims are provided. In the following description, reference is made to the accompanying drawings, which form a part hereof, and in which there is shown by way of illustration, a preferred embodiment of the invention. Such embodiment also does not define the scope of the invention and reference must be made therefore to the claims for this purpose.

We claim:

1. A method of data acquisition in a computed tomography machine 10 having an opposed x-ray source 16 and multi-row x-ray detector 22 mounted on a gantry 12 for helical rotation about a patient along a longitudinal axis, the method comprising the steps of:
   (a) determining a longitudinal variation in x-ray detection 34 across at least two rows 24 of the multi-row x-ray detector;
   (b) acquiring with the multi-row x-ray detector, a set of tomographic projections data at a plurality of angles about the patient, over a helical path with respect to the patient, for detector elements 20 of the rows of the multi-row x-ray detector;
   (c) selecting a slice 36 having a location and thickness for a tomographic reconstruction;
   (d) for each of the rows, weighting the data of the detector elements of the row according to the determined variation in x-ray detection of the row and according to an overlap of the slice with the row;
   (e) reconstructing a tomographic image from the weighted data.

2. The method of claim 1 wherein in step (d) the weighting of the data of the detector elements of the row provides for interpolation between corresponding detector elements of the two row to the slice location during the step of reconstructing.

3. The method of claim 1 including further after step (d) and before step (e) the step of interpolating the weighted data between corresponding detector elements of the two rows to the slice location.

4. The method of claim 1 wherein the longitudinal variation in x-ray detection is determined by approximation with an irregular trapezoid.

5. The method of claim 1 wherein the longitudinal variation in x-ray detection is determined by approximation with a Gaussian curve.

6. The method of claim 1 wherein the longitudinal variation in x-ray detection is determined by measurements held in a stored template.

7. The method of claim 1 wherein the multi-row x-ray detector has more than two rows.

8. The method of claim 7 wherein the two rows of the multi-row x-ray detector are adjacent rows.

9. The method of claim 8 including the step of placing an opaque mask along the interface between the two rows.

10. The method of claim 1 including the step of collimating the x-ray beam to a longitudinal dimension such that a collimation shadow falls on the mutual outer edges of the two rows.

11. The method of claim 1 wherein the slice thickness is less than a longitudinal dimension of one row.

12. The method of claim 3 wherein the interpolation of the weighted data is a linear interpolation.

13. In a computed tomography machine having an x-ray source mounted on a gantry for helical rotation about a patient along a longitudinal axis, a slice interpolation system comprising:
   (a) a multi-row x-ray detector mounted opposite the x-ray source to provide a set of tomographic projections data at a plurality of angles about the patient, over a helical path with respect to the patient, from detector elements of the rows of the multi-row x-ray detector;

(b) a selector designating a slice location and thickness for a tomographic reconstruction;

(c) a weighter communicating with the memory and selector and weighting the data of the detector elements of the row according to a determined longitudinal variation in x-ray detection of the row; and (d) a reconstructor generating a tomographic image from the weighted from the interpolator.

14. The slice interpolation system of claim 13 wherein the weighter further weights the data of the detector elements of the row provides for interpolation between corresponding detector elements of the two row to the slice location during the step of reconstructing.

15. The slice interpolation system of claim 13 including further an interpolator interpolating the weighted data between corresponding detector elements of the two rows to the slice location.

16. The slice interpolation system of claim 13 wherein longitudinal variation in x-ray detection is determined from an irregular trapezoidal model.

17. The slice interpolation system of claim 13 wherein longitudinal variation in x-ray detection is determined from a Gaussian curve model.

18. The slice interpolation system of claim 13 wherein the longitudinal variation in x-ray detection is determined from a stored template of measured values.

19. The slice interpolation system of claim 13 wherein the multi-row x-ray detector has more than two rows.

20. The slice interpolation system of claim 15 wherein the two rows of the multi-row x-ray detector are adjacent rows.

21. The slice interpolation system of claim 20 wherein the multi-row detector includes an opaque mask along the interface between the two rows.

22. The slice interpolation system of claim 13 wherein the x-ray beam is collimated to a longitudinal dimension such that a collimation shadow falls on the mutual outer edges of the two rows.

23. The slice interpolation system of claim 13 wherein the slice thickness is less than a longitudinal dimension of one row.

24. The slice interpolation system of claim 13 wherein the interpolator interpolates the weighted data using a linear interpolation.

* * * * *

UNITED STATES PATENT AND TRADEMARK OFFICE
CERTIFICATE OF CORRECTION

PATENT NO.    : 6,359,956 B1
DATED         : March 19, 2002
INVENTOR(S)   : Hsieh et al.

It is certified that error appears in the above-identified patent and that said Letters Patent is hereby corrected as shown below:

Column 3,
Line 15, "7" should be -- $\gamma$ --.

Signed and Sealed this

Twenty-second Day of October, 2002

Attest:

JAMES E. ROGAN
Attesting Officer    Director of the United States Patent and Trademark Office